(12) United States Patent
Park (10) Patent No.: US 11,576,875 B2
(45) Date of Patent: Feb. 14, 2023

(54) COMPOSITION COMPRISING ETHYL VANILLIN AS EFFECTIVE INGREDIENT FOR EXHIBITING EFFECT OF MUSCLE STRENGTHENING, MUSCLE ENHANCEMENT, MUSCLE DIFFERENTIATION, MUSCLE REGENERATION, OR SARCOPENIA SUPPRESSION

(71) Applicant: INDUSTRY-ACADEMIC COOPERATION FOUNDATION, YONSEI UNIVERSITY, Seoul (KR)

(72) Inventor: Tae Sun Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 234 days.

(21) Appl. No.: 16/631,761

(22) PCT Filed: Jul. 17, 2018

(86) PCT No.: PCT/KR2018/008071
§ 371 (c)(1),
(2) Date: Jan. 16, 2020

(87) PCT Pub. No.: WO2019/017676
PCT Pub. Date: Jan. 24, 2019

(65) Prior Publication Data
US 2020/0170964 A1   Jun. 4, 2020

(30) Foreign Application Priority Data
Jul. 18, 2017   (KR) .................. 10-2017-0090885

(51) Int. Cl.
*A61K 31/11* (2006.01)
*A23K 20/111* (2016.01)
*A23L 33/10* (2016.01)
*A61P 21/06* (2006.01)
*A61P 21/04* (2006.01)

(52) U.S. Cl.
CPC ............ *A61K 31/11* (2013.01); *A23K 20/111* (2016.05); *A23L 33/10* (2016.08); *A61P 21/04* (2018.01); *A61P 21/06* (2018.01)

(58) Field of Classification Search
CPC ....... A61K 31/11; A23K 20/111; A23L 33/10; A61P 21/04; A61P 21/06
See application file for complete search history.

(56) References Cited

U.S. PATENT DOCUMENTS

2003/0049208 A1   3/2003   Ream et al.
2006/0240131 A1   10/2006   Warrenburg et al.

FOREIGN PATENT DOCUMENTS

| EP | 1430901 | 6/2004 |
|---|---|---|
| JP | 2013245164 | 12/2013 |
| KR | 20100094485 | 8/2010 |
| KR | 101006556 | 1/2011 |
| KR | 20130132473 | 12/2013 |
| KR | 20150014307 | 2/2015 |
| KR | 20160003968 | 1/2016 |
| KR | 20170022427 | 3/2017 |

OTHER PUBLICATIONS

Nigel G. Liang, Critical Reviews in Clinical Laboratory Sciences, 2012; 49(2): 33-48. (Year: 2012).*
Bodine et al., Akt/mTOR Pathway is a Crucial Regulator of Skeletal Muscle Hypertrophy and Can Prevent Muscle Atrophy In Vivo, *Nature Cell Biology*, 3: 1014-1019, 2001.
Gumucio, et al., "Atrogin-1, MuRF-1, and Sarcopenia," *Endocrine*, 43(1): 12-21, 2013.
International Search Report and Written Opinion Issued in Corresponding PCT Patent Application No. PCT/KR2018/008071, dated Jan. 2, 2019.
Jung, et al., "Assessment of the Anti-Angiogenic, Anti-Inflammatory and Anti-Nociceptive Properties of Ethyl Vanillin," *Archives of Pharmacal Research*, 33(2): 309-316, 2010.
Tai, et al. "Antioxidant Properties of Ethyl Vanillin In Vitro and In Vivo." *Bioscience, Biotechnology, and Biochemistry*, 75: 2346-2350, 2011.
Yemis, et al., "Effect of Vanillin, Ethyl Vanillin, and Vanillic Acid on the Growth and Heat Resistance of Cronobacter Species," *Journal of Food Protection*, 74(12): 2062-2069, 2011.

* cited by examiner

Primary Examiner — Jeffrey S Lundgren
Assistant Examiner — William Y Lee
(74) Attorney, Agent, or Firm — Norton Rose Fulbright US LLP (57) ABSTRACT

The present invention relates to a composition comprising ethyl vanillin or a pharmaceutically acceptable salt thereof as an effective ingredient for preventing or treating muscle disease or for improving a muscle function. Having the capability of upregulating the expression of a protein associated with muscle protein synthesis and muscle mass increase in myocytes and downregulating at an mRNA level the expression of an enzyme involved in muscle protein degradation, ethyl vanillin can exhibit effects of muscle differentiation, muscle regeneration, and muscle strengthening through an increase in muscle mass against muscle diseases attributed to muscle function decrease, muscle consumption, or muscle degradation and can suppress sarcopenia. Thus, ethyl vanillin can be used for preventing or treating muscle diseases or for promoting muscle differentiation, muscle regeneration and muscle strengthening, muscle mass increase, or muscle generation or for improving muscle function.

14 Claims, 4 Drawing Sheets
Specification includes a Sequence Listing.

SEQUENCE LISTING

<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: MaFbx_F primer
<400> SEQUENCE: 1
gtccagagag tcggcaagtc                                       20

<210> SEQ ID NO 2
<211> LENGTH: 20
<212> TYPE: DNA
<213> ORGANISM: Artificial
<220> FEATURE:
<223> OTHER INFORMATION: MaFbx_R primer
<400> SEQUENCE: 2
gtcggtgatc gtgagacctt                                       20

<210> SEQ ID NO 3
<211> LENGTH: 20
<212> TYPE: DNA
<213> ORGANISM: Artificial
<220> FEATURE:
<223> OTHER INFORMATION: MuRF1_F primer
<400> SEQUENCE: 3
acatctactg tctcacgtgt                                       20

<210> SEQ ID NO 4
<211> LENGTH: 20
<212> TYPE: DNA
<213> ORGANISM: Artificial
<220> FEATURE:
<223> OTHER INFORMATION: MuRF1_R primer
<400> SEQUENCE: 4
tgtccttgga agatgctttg                                       20

<210> SEQ ID NO 5
<211> LENGTH: 20
<212> TYPE: DNA
<213> ORGANISM: Artificial
<220> FEATURE:
<223> OTHER INFORMATION: Myostatin_F primer
<400> SEQUENCE: 5
tcacgctacc acggaaacaa                                       20

<210> SEQ ID NO 6
<211> LENGTH: 20
<212> TYPE: DNA
<213> ORGANISM: Artificial
<220> FEATURE:
<223> OTHER INFORMATION: Myostatin_R primer
<400> SEQUENCE: 6
aggagtcttg acgggtctga                                       20

<210> SEQ ID NO 7
<211> LENGTH: 20
<212> TYPE: DNA
<213> ORGANISM: Artificial

```
<220> FEATURE:
<223> OTHER INFORMATION: IGF_F primer

<400> SEQUENCE: 7
ggggactttc gtgactgagc                                                 20

<210> SEQ ID NO 8
<211> LENGTH: 20
<212> TYPE: DNA
<213> ORGANISM: Artificial
<220> FEATURE:
<223> OTHER INFORMATION: IGF_R primer

<400> SEQUENCE: 8
ggtaggtccg ggtcgtttac                                                 20

<210> SEQ ID NO 9
<211> LENGTH: 20
<212> TYPE: DNA
<213> ORGANISM: Artificial
<220> FEATURE:
<223> OTHER INFORMATION: GAPDH_F primer

<400> SEQUENCE: 9
gtgatggcat ggactgtggt                                                 20

<210> SEQ ID NO 10
<211> LENGTH: 20
<212> TYPE: DNA
<213> ORGANISM: Artificial
<220> FEATURE:
<223> OTHER INFORMATION: GAPDH_R primer

<400> SEQUENCE: 10
ggagccaaaa gggtcatcat                                                 20
```

COMPOSITION COMPRISING ETHYL VANILLIN AS EFFECTIVE INGREDIENT FOR EXHIBITING EFFECT OF MUSCLE STRENGTHENING, MUSCLE ENHANCEMENT, MUSCLE DIFFERENTIATION, MUSCLE REGENERATION, OR SARCOPENIA SUPPRESSION

CROSS-REFERENCE TO RELATED APPLICATIONS

This application is a national phase application under 35 U.S.C. § 371 of International Application No. PCT/KR2018/008071, filed Jul. 17, 2018, which claims priority to and the benefit of Korean Patent Application No. 10-2017-0090885, filed on Jul. 18, 2017, the disclosures of which are incorporated herein by reference in their entirety.

TECHNICAL FIELD

The present invention relates to a pharmaceutical composition for preventing or treating a muscle disease, which comprises, as an active ingredient, ethyl vanillin or a pharmaceutically acceptable salt thereof.

BACKGROUND ART

In 2000, the elderly population in South Korea accounted for 7.2% of the total population and thus Korea has entered an aging society, and is expected to enter a super-aging society in 2050 (2013 elderly statistics, the National Statistical Office). Muscle mass in humans decreases with age (about 10-15% at an age of 50-70 years, and 30% or more decrease at an age of 70-80 years), and accordingly, muscle strength and muscle function are also weakened, which is referred to as age-related sarcopenia. Age-related sarcopenia is a major cause of limiting the independent living of the elderly by inducing activity disorders and gait disturbances. In addition, sarcopenia lowers a basal metabolic rate, increases insulin resistance, promotes type 2 diabetes, and increases the risk of hypertension and cardiovascular disease by 3-5 times. Currently, no drug has been approved for the treatment of sarcopenia, and drug repositioning technology is being developed to apply a myostatin inhibitor or other FDA-approved agents for the treatment of diseases to sarcopenia.

Muscles are divided into skeletal muscles, cardiac muscles, and visceral muscles, and thereamong, skeletal muscles are the most abundant tissues in the human body, accounting for 40-45% of body weight. Skeletal muscles are attached to the bone by tendons, creating bone movement or force. One muscle is made up of numerous myofibers, which in turn are made up of numerous myofibrils consisting of actin and myosin. When actin and myosin move by overlapping each other, the length of muscles shortens or increases, causing overall muscle contraction and relaxation. An increase in myofibril size means an increase in myofiber thickness, resulting in an increase in muscle.

The type of myofibers that constitute muscles is mainly classified into Type I, Type IIA, and Type IIB by a metabolic process and a contraction rate that produce ATP. "Type I myofibers" have a low contraction rate and contain a large number of myoglobin and mitochondria, which are suitable for sustained, low-intensity aerobic activity. Type I myofibers have a red color and are also called red muscles, and the soleus is typical. Meanwhile, "Type IIB myofibers" are very short, but are used for high-intensity anaerobic exercise due to a high contraction rate thereof, and contain a low amount of myoglobin, thus having a white color. "Type IIA myofibers" have characteristics between the aforementioned two myofibers. With age, not only does the composition of Type I and II myofibers for each muscle site vary, but all types of myofibers are also reduced.

Skeletal muscles have the characteristics of being regenerated and maintained according to the environment, but these characteristics are lost with age, and consequently, as aging progresses, muscle mass is reduced and muscle strength is also lost. As a signaling system involved in muscle growth and regeneration, there is signaling which is mediated by insulin like growth factor 1 (IGF-1)/AKT to regulate protein synthesis. The activation of an IGF-1 receptor (IGF-1R) present in the muscle cell membrane increases AKT phosphorylation through IRS1 and PI3K phosphorylation, and the latter activates mTORC phosphorylation. The activation of mTORC increases the phosphorylation of ribosomal protein S6 kinase beta-1 (p70S6K1), thereby not only increasing mRNA translation, but also increasing the activity of eukaryotic translation initiation factor 4 G (eIF4G) and phosphorylating eukaryotic translation initiation factor 4E binding protein 1 (4E-BP1). eIF4G and 4E-BP1 are involved in the formation of an eIF4F complex. That is, eIF4G binds to eIF4A and eIF4E to form an eIF4F complex, while phosphorylation of 4E-BP1 inhibits binding capacity for eIF4E, leading to an increase in free eIF4E. The latter combines with other translation initiation factors (eIF4G and eIF4A) to form an eIF4F complex, which in turn promotes translation initiation by stabilizing ribosomal structures, ultimately increasing protein synthesis (Bodine et al., Akt/mTOR pathway is a crucial regulator of skeletal muscle hypertrophy and can prevent muscle atrophy in vivo. Nature Cell Biology, 3, 1014-1019, 2001).

In addition, AKT phosphorylation stimulates myofiber growth by increasing eIF2B expression through glycogen synthase kinase 3 (GSK3) and also inhibits muscle loss by inhibiting the expression of forkhead box O (FOXO), which is a proteolytic transcription factor. Muscle loss is regulated by signaling mediated by receptors of the TGF-family, including myostatin, transforming growth factor beta (TGF-β), and activin. The binding of a ligand to TGF-β type II receptor phosphorylates a Type I receptor, and the latter phosphorylates the smad 2/3 complex and eventually activates FOXO. The latter increases the gene expression of muscle-specific ubiquitin-ligases, i.e., muscle RING-finger protein-1 (MURF1) and muscle atrophy F-Box (MAFbx)/atrogin-1, which attach ubiquitin to the lysine site of a target protein to promote proteolysis, eventually leading to muscle loss (Gumucio et al., Atrogin-1, MuRF-1, and sarcopenia. Endocrine, 43, 12-21, 2013).

Meanwhile, ethyl vanillin is registered as a flavoring agent in the European Council of Europe (COE), the Korean Food Additives Codex (KFAC), and the US Food and Drug Association (FDA) food additive database and is used as an adjuvant or the like, and is registered in the cosmetic ingredients list of the Korean Cosmetic Association for use as a sweetening agent of cosmetics or for mixing of fragrances. To date, ethyl vanillin is known to exhibit antioxidant and antimicrobial physiological activity (Non-Patent Document 1 and Non-Patent Document 2), and when administered via a route such as oral administration, transdermal administration, or the like, it has been reported that ethyl vanillin does not induce toxicity in vivo and can also exhibit significant biological activity (Non-Patent Documents 1 to 4).

Therefore, as a result of having determined that demand for a pharmaceutical composition, health functional food, or cosmetic composition that prevents muscle loss and exhibits a muscle function enhancement effect would continuously increase in modern societies in which aging continues and having screened an active compound capable of exhibiting a muscle function enhancement effect, the inventors of the present invention confirmed that ethyl vanillin could exhibit a muscle function enhancement effect and a muscle synthesis enhancement effect in muscle cells.

(Non-Patent Document 1) Tai et al. "Antioxidant Properties of Ethyl Vanillin in vitro and in vivo." Bioscience, Biotechnology, and Biochemistry 75. 2346-2350. 2011

(Non-Patent Document 2) Yemi et al. "Effect of vanillin, ethyl vanillin, and vanillic acid on the growth and heat resistance of Cronobacter species." Journal of Food Protection®74. 2062-2069. 2011

(Non-Patent Document 3) American Pharmaceutical Association. Journal of the American Pharmaceutical Association. American Pharmaceutical Association 1. 1912

(Non-Patent Document 4) Monsanto Co., 1991a. Final report of several tests with ethavan with cover letter dated 112191. EPA Doc 86-920000149, microfiche no. OTS0534355. Date Aug. 17, 1976. Unpublished report submitted by EFFA to FLAVIS Secretariat

SUMMARY OF THE INVENTION

The present invention provides a pharmaceutical composition for preventing or treating a muscle disease, comprising ethyl vanillin or a pharmaceutically acceptable salt thereof as an active ingredient.

Another object of the present invention is to provide a health functional food composition or livestock feed composition for the prevention or alleviation of a muscle disease, muscle differentiation promotion, muscle regeneration, muscle function improvement, or muscle strengthening, the composition comprising ethyl vanillin or a pharmaceutically acceptable salt thereof as an active ingredient.

Another object of the present invention is to provide a cosmetic composition for improving muscle function, comprising an ethyl vanillin derivative or a pharmaceutically acceptable salt thereof as an active ingredient.

Another object of the present invention is to provide a method of preventing or treating a muscle disease, promoting muscle differentiation, regenerating muscles, or strengthening muscles, the method comprising administrating, to a subject, a pharmaceutical composition comprising an ethyl vanillin derivative or a salt thereof as an active ingredient, or allowing it to be taken.

Another object of the present invention is to provide a use of a composition for the prevention or treatment of a muscle disease, muscle differentiation promotion, muscle regeneration, or muscle strengthening, the composition comprising an ethyl vanillin derivative or a salt thereof as an active ingredient.

However, technical problems to be solved by the present invention are not limited to the above-described technical problems, and other unmentioned technical problems will become apparent from the following description to those of ordinary skill in the art.

According to an aspect of the present invention, there is provided a pharmaceutical composition for preventing or treating a muscle disease, comprising ethyl vanillin or a pharmaceutically acceptable salt thereof as an active ingredient.

According to one embodiment of the present invention, the ethyl vanillin may be a compound having a structure of Formula 1 below:

[Formula 1]

According to one embodiment of the present invention, the composition may increase the expression of the p-4E-BP1 protein and the p-p70S6K1 protein.

According to one embodiment of the present invention, the composition may reduce the expression of muscle RING-finger protein-1 (MuRF1), muscle atrophy F-box (MaFbx), or myostatin.

According to one embodiment of the present invention, the muscle disease may be a muscle disease caused by muscle dysfunction, muscle loss, muscle atrophy, muscle wasting, or muscle degeneration, and more particularly, may be any one or more selected from the group consisting of atony, muscular atrophy, muscular dystrophy, myasthenia, cachexia, rigid spine syndrome, amyotrophic lateral sclerosis (Lou Gehrig's disease), Charcot-Marie-Tooth disease, and sarcopenia.

The present invention also provides a pharmaceutical composition for muscle differentiation promotion, muscle regeneration, or muscle strengthening, comprising ethyl vanillin or a pharmaceutically acceptable salt thereof as an active ingredient.

The present invention also provides a health functional food composition for preventing or alleviating a muscle disease, comprising ethyl vanillin or a pharmaceutically acceptable salt thereof as an active ingredient. The present invention also provides a health functional food composition for muscle differentiation promotion, muscle regeneration, muscle function improvement, or muscle strengthening, comprising ethyl vanillin or a pharmaceutically acceptable salt thereof as an active ingredient.

The present invention also provides a pharmaceutical composition for increasing muscle mass or promoting myogenesis, comprising ethyl vanillin or a pharmaceutically acceptable salt thereof as an active ingredient.

The present invention also provides a health functional food composition for increasing muscle mass or promoting myogenesis, comprising ethyl vanillin or a pharmaceutically acceptable salt thereof as an active ingredient.

The present invention also provides a health functional food composition for muscle function improvement, comprising ethyl vanillin or a pharmaceutically acceptable salt thereof as an active ingredient.

The present invention also provides a livestock feed composition for preventing or alleviating a muscle disease, comprising ethyl vanillin or a pharmaceutically acceptable salt thereof as an active ingredient.

The present invention also provides a livestock feed composition for muscle differentiation promotion, muscle regeneration, muscle function improvement, or muscle strengthening, comprising ethyl vanillin or a pharmaceutically acceptable salt thereof as an active ingredient.

The present invention also provides a cosmetic composition for muscle function improvement, comprising ethyl vanillin or a pharmaceutically acceptable salt thereof as an active ingredient.

According to another aspect of the present invention, there is provided a method of preventing or treating a muscle disease, promoting muscle differentiation, regenerating muscles, or strengthening muscles, comprising administering, to a subject, a pharmaceutical composition comprising an ethyl vanillin derivative or a pharmaceutically acceptable salt thereof as an active ingredient, or allowing it to be taken.

According to still another aspect of the present invention, there is provided a use of a composition for preventing or treating a muscle disease, promoting muscle differentiation, regenerating muscles, or strengthening muscles, the composition comprising an ethyl vanillin derivative or a pharmaceutically acceptable salt thereof as an active ingredient.

The present invention relates to a composition for preventing or treating a muscle disease, or improving muscle function, comprising ethyl vanillin or a pharmaceutically acceptable salt thereof as an active ingredient, and the ethyl vanillin can increase the expression of proteins related to myoprotein synthesis and a muscle mass increase in muscle cells, and can inhibit the expression of a myoprotein degradation-related enzyme at an mRNA level. Thus, the composition can exhibit a muscle strengthening effect through muscle differentiation, muscle regeneration, and a muscle mass increase in muscle diseases caused by muscle dysfunction, muscle loss, or muscle degeneration, and can inhibit muscle loss, and thus can be used for the prevention or treatment of a muscle disease, muscle differentiation, muscle regeneration, muscle strengthening, a muscle mass increase, myogenesis promotion, or muscle function improvement.

DETAILED DESCRIPTION OF THE INVENTION

Hereinafter, terms as used in the present invention will be described.

The term "ethyl vanillin" as used herein refers to a phenolic aldehyde-based material having the molecular formula of $C_9H_{10}O_3$. The ethyl vanillin has a molecular weight of 166.18 g/mol and has a structure of Formula 1 below:

[Formula 1]

The IUPAC name of ethyl vanillin is 3-ethoxy-4-hydroxybenzaldehyde, and is also called bourbonal or the like as another name.

Ethyl vanillin is present in the form of white or light white powder at room temperature, and is insoluble in water and soluble in chloroform and ethanol. Ethyl vanillin is known as a fragrance ingredient, and the fragrance family is known to have vanilla, specifically sweet, creamy, vanilla, and caramel odor flavors.

The term "muscle" as used herein collectively refers to tendon, muscle, and sinew, and "muscle function" means the ability of muscle to exert a force through muscle contraction, and encompasses: muscle strength, which is the ability of muscle to exert maximum contraction to overcome resistance; muscular endurance, which is the ability to indicate how long or how many times muscle can repeat contraction and relaxation at a given weight; and explosive muscular strength, which is the ability to exert a strong force within a short period of time. Such muscle functions are proportional to muscle mass, and "muscle function improvement" means the act of making muscle functions better.

Hereinafter, the present invention will be described in detail.

Pharmaceutical Composition for Prevention or Treatment of Muscle Disease The present invention provides a pharmaceutical composition for the prevention or treatment of a muscle disease, comprising ethyl vanillin or a pharmaceutically acceptable salt thereof as an active ingredient.

The present invention also provides a pharmaceutical composition for muscle differentiation promotion, muscle regeneration, or muscle strengthening, comprising ethyl vanillin or a pharmaceutically acceptable salt thereof as an active ingredient.

The present invention also provides a pharmaceutical composition for increasing muscle mass or promoting myogenesis, comprising ethyl vanillin or a pharmaceutically acceptable salt thereof as an active ingredient.

In the pharmaceutical composition of the present invention, the ethyl vanillin may be a compound having a structure of Formula 1 below, but the present invention is not limited thereto, and any isomer, hydrate, or derivative having activity that is the same as or similar to that of ethyl vanillin within a range that can be understood by those of ordinary skill in the art is applicable:

[Formula 1]

A method of obtaining the ethyl vanillin is not particularly limited, and the ethyl vanillin may be isolated from a plant containing the ethyl vanillin or chemically synthesized using a known method, or commercially available ethyl vanillin may be used.

In the pharmaceutical composition of the present invention, the ethyl vanillin or pharmaceutically acceptable salt thereof may increase the expression of the p-4E-BP1 protein and the p-p70S6K1 protein, and may reduce the expression of muscle RING-finger protein-1 (MuRF1), muscle atrophy F-box (MaFbx), or myostatin. In particular, representative molecules related to protein synthesis include p70S6K1, 4E-BP1, and eIF members, and the activity of these three molecules is regulated by higher mTORCs. The activation of mTORc phosphorylates p70S6K1, and the activated p70S6K1 phosphorylates 40S ribosomal protein S6 to increase mRNA translation. In addition, the activation of mTORC not only increases the activity of eIF4G, but also phosphorylates 4E-BP1, and both molecules are involved in forming an eIF4F complex. That is, eIF4G binds to eIF4A and eIF4E to form an eIF4F complex, while, when 4E-BP1 is phosphorylated, the ability thereof to bind to eIF4E is inhibited, increasing eIF4E in a free state. The latter binds to other translation initiation factors (eIF4G and eIF4A) to form an eIF4F complex, which in turn promotes translation initiation by stabilizing the ribosomal structures, ultimately increasing protein synthesis. MAFbx/Atrogin-1 and MuRF1 are muscle-specific ubiquitin-ligases, which are representative proteins that promote proteolysis by attaching ubiquitin to the lysine site of a target protein, and induce muscle loss. The pharmaceutical composition according to the present invention may reduce the expression of muscle RING-finger protein-1 (MuRF1) or muscle atrophy F-box (MaFbx), thereby inhibiting muscle loss.

In the pharmaceutical composition of the present invention, the muscle disease includes muscle diseases caused by muscle dysfunction, muscle loss, muscle atrophy, muscle wasting, or muscle degeneration. In particular, the muscle disease may be any one or more selected from the group consisting of atony, muscular atrophy, muscular dystrophy, myasthenia, cachexia, rigid spine syndrome, amyotrophic lateral sclerosis (Lou Gehrig's disease), Charcot-Marie-Tooth disease, and sarcopenia, but the present invention is not limited thereto. In addition, the muscle wasting or degeneration is caused by whole factors, acquired factors, aging, and the like, and muscle wasting is characterized by the gradual loss of muscle mass, and weakness and degeneration of muscles, especially skeletal or voluntary muscles and cardiac muscles.

In addition, in view of the fact that the pharmaceutical composition of the present invention is used for muscle differentiation promotion, muscle regeneration, or muscle strengthening, the differentiation of myocytes means induction of a muscle developmental program that specifies components of myofibers such as contractile organs (myofibril). A useful therapeutic agent for differentiation increases the amount of all myofibril components present in diseased tissues by about 10% or more, more preferably 50% or more, and most preferably 100% or more, compared to equivalent tissues present in similarly treated control animals.

In addition, in view of the fact that the pharmaceutical composition of the present invention is used for muscle differentiation promotion, muscle regeneration, or muscle strengthening or is used to increase muscle mass, muscle growth may occur by increasing the fiber size and/or by increasing the number of fibers. The growth of muscles may be measured by A) increasing a wet weight, B) increasing a protein content, C) increasing the number of myofibers, and D) increasing the diameter of myofibers. An increase in myofiber growth may be defined as an increase in diameter when the diameter is defined as the minor axis of a sectional ellipsoid. A useful therapeutic agent increases the wet weight, the protein content, and/or diameter by 10% or more, more preferably 50% or more, and most preferably 100% or more in animals that had muscle degenerated by about at least 10% compared to control animals that had previously been treated similarly (i.e., animals with degenerated muscle tissue not treated with a muscle growth compound). A compound for increasing growth by increasing the number of myofibers is useful as a therapeutic agent when increasing the number of myofibers in diseased tissue by at least 1%, more preferably at least 20%, and most preferably at least 50%. These percentage values are determined relative to the basal level in untreated and disease-free comparative mammals when the compound is administered and acts locally, or in non-contralateral adult diseased muscles.

In addition, in view of the fact that the pharmaceutical composition of the present invention is used for muscle differentiation promotion, muscle regeneration, or muscle strengthening, muscle regeneration means the process by which new myofibers are formed from myoblasts. A useful therapeutic agent for regeneration increases the number of new fibers by about at least 1%, more preferably at least 20%, and most preferably, at least 50% as described above.

The differentiation of myocytes means induction of a muscle developmental program that specifies components of myofibers such as contractile organs (myofibril). A useful therapeutic agent for differentiation increases the amount of all myofibril components present in diseased tissues by about 10% or more, more preferably 50% or more, and most preferably 100% or more, compared to equivalent tissues present in similarly treated control animals.

In addition, in view of the fact that the pharmaceutical composition of the present invention is used for muscle mass increase or myogenesis promotion, "muscle mass increase" is to improve the growth of body components, especially muscles, and may include an increase in muscle mass through physical exercise and improved endurance, and an increase in muscle mass using a method of administering, into the body, a material having an effect of increasing muscles, and the type of muscles is not limited.

In particular, according to one embodiment of the present invention, when mouse myoblasts reduced by dexamethasone were treated with ethyl vanillin, it can be confirmed that the number of myotubes of the mouse myoblasts was significantly increased. That is, the ethyl vanillin according to the present invention may increase the thickness of myotubes in mouse myoblasts, thereby inhibiting muscle loss and promoting the growth of muscles.

In addition, when mouse myoblasts reduced by dexamethasone are treated with ethyl vanillin, it can be confirmed that the ethyl vanillin not only significantly increases the expression of the p-4E-BP1 and p-p70S6K1 proteins associated with protein synthesis, but also significantly reduces the expression of MuRF1 and Mafbx/atrogin 1, which are proteins that induce muscle reduction. That is, the ethyl vanillin according to the present invention may increase the phosphorylation of the 4E-BP1 protein and the p70S6K protein in mouse myoblasts, and may increase muscle mass by inhibiting the gene expression of MuRF1 and Mafbx/atrogin 1.

In the pharmaceutical composition of the present invention, the amount of the active ingredient is not particularly limited as long as it includes ethyl vanillin or a pharmaceutically acceptable salt thereof, and preferably, the ethyl vanillin may be included at a concentration of 0.1 μM to 1,000 μM, but the present invention is not limited thereto. In this regard, when the concentration of the ethyl vanillin is less than the above range, protein synthesis and degradation activity in myocytes are reduced such that it is difficult to exhibit the effect of preventing or treating a muscle disease. When the concentration of the ethyl vanillin is greater than the above range, there may be concerns about toxicity including cytotoxicity.

The ethyl vanillin of the present invention may be used in the form of a pharmaceutically acceptable salt, and the salt may be an acid addition salt formed by a pharmaceutically acceptable free acid. The acid addition salt is obtained from: inorganic acids such as hydrochloric acid, nitric acid, phosphoric acid, sulfuric acid, hydrobromic acid, hydriodic acid, nitrous acid, and phosphorous acid; or nontoxic organic acids such as aliphatic mono- and dicarboxylates, phenyl-substituted alkanoates, hydroxy alkanoates and alkandioates, aromatic acids, and aliphatic and aromatic sulfonic acids. Examples of these pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitro benzoates, hydroxybenzoates, methoxybenzoates, phthalates, terephthalates, benzene sulfonates, toluene sulfonates, chlorobenzene sulfonates, xylene sulfonates, phenyl acetates, phenylpropionates, phenylbutyrates, citrates, lactates, β-hydroxybutyrates, glycolates, maleates, tartrates, methanesulfonates, propanesulfonates, naphthalene-1-sulfonates, naphthalene-2-sulfonates, and mandelates.

Acid addition salts according to the present invention may be prepared using a conventional method, for example, by dissolving the ethyl vanillin in an excess of an aqueous acid solution and precipitating the salt using a water-miscible organic solvent, e.g., methanol, ethanol, acetone, or acetonitrile, or may also be prepared by heating the same amount of ethyl vanillin and an acid or alcohol in water, and then evaporating and drying the resulting mixture or suction-filtering the precipitated salt.

In addition, pharmaceutically acceptable metallic salts may be prepared by using bases. Alkali metal or alkaline earth metal salts are obtained by, for example, dissolving a compound in an excess of an alkali metal hydroxide or alkaline earth metal hydroxide solution, filtering a non-soluble compound salt, and evaporating and drying the filtrate. At this time, it is pharmaceutically preferable that a sodium salt, a potassium salt, or a calcium salt is prepared as a metal salt. In addition, silver salts corresponding thereto are obtained by reacting an alkali metal or an alkaline earth metal salt with a suitable silver salt (e.g., silver nitrate). Moreover, the ethyl vanillin of the present invention includes not only pharmaceutically acceptable salts thereof, but also all salts, hydrates, and solvates that may be prepared using general methods.

Addition salts according to the present invention may be prepared using general methods, for example, by dissolving ethyl vanillin in a water-miscible organic solvent, e.g., acetone, methanol, ethanol, acetonitrile, or the like, adding an excess of an organic acid or an aqueous inorganic acid solution thereto, and then precipitating or crystalizing the resulting solution. Subsequently, the solvent or the excess of the acid may be evaporated from the mixture, followed by drying, thereby obtaining an addition salt, or the precipitated salt may be subjected to suction filtration.

The pharmaceutical composition of the present invention may be in the form of various oral or parenteral formulations. When the composition is formulated, one or more of buffers (e.g., saline or PBS), antioxidants, bacteriostatic agents, chelating agents (e.g., EDTA or glutathione), fillers, extenders, binders, adjuvants (e.g., aluminum hydroxide), suspending agents, thickening agents, wetting agents, disintegrating agents or surfactants, diluents, or excipients may be used.

Examples of solid preparations for oral administration include tablets, pills, powders, granules, capsules, and the like, and these solid preparations are formulated by mixing one or more compounds with at least one excipient, for example, starch (including corn starch, wheat starch, rice starch, potato starch, and the like), calcium carbonate, sucrose, lactose, dextrose, sorbitol, mannitol, xylitol, erythritol, maltitol, cellulose, methyl cellulose, sodium carboxymethylcellulose and hydroxypropylmethyl-cellulose, gelatin, or the like. For example, tablets or sugar-coated tablets may be obtained by mixing an active ingredient with a solid excipient, pulverizing the mixture, adding a suitable adjuvant thereto, and then formulating the resultant mixture into a granular mixture.

In addition to simple excipients, lubricants such as magnesium stearate, talc, and the like are also used. Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance agent, a preservative, and the like. In addition, in some embodiments, crosslinked polyvinylpyrrolidone, agar, alginic acid, sodium alginate, or the like may be added as a disintegrating agent, and these preparations may further include an anticoagulant, a lubricant, a wetting agent, a flavoring, an emulsifier, a preservative, and the like.

Preparations for parenteral administration include an aqueous sterile solution, a non-aqueous solvent, a suspension, an emulsion, a freeze-dried preparation, a suppository, or the like. Non-limiting examples of the non-aqueous solvent and the suspension solvent include propylene glycol, polyethylene glycol, a vegetable oil such as olive oil, and an injectable ester such as ethyl oleate. Examples of suppository bases include Witepsol, Macrogol, Tween 61, cacao butter, laurin, glycerol, gelatin, and the like.

The pharmaceutical composition of the present invention may be administered orally or parenterally, and for parenteral administration, the pharmaceutical composition of the present invention may be formulated using a method known in the art into the form of: a dermatologic agent; an injection for intraperitoneal injection, intrarectal injection, intravenous injection, intramuscular injection, subcutaneous injection, intrauterine dural injection, or intracerebrovascular injection; a transdermal delivery agent; or a nasal inhalant.

Such injections must be sterile and protected from contamination of microorganisms such as bacteria and fungi. Non-limiting examples of suitable carriers for injections include solvents or dispersion media including water, ethanol, polyols (e.g., glycerol, propylene glycol, liquid polyethylene glycol, and the like), mixtures thereof and/or vegetable oils. More preferably, suitable carriers include isotonic solutions such as Hanks' solution, Ringer's solution, phosphate buffered saline (PBS) containing triethanolamine or sterile water for injection, 10% ethanol, 40% propylene glycol, and 5% dextrose, and the like. To protect the injections from microbial contamination, various antibacterial and antifungal agents such as parabens, chlorobutanol, phenol, sorbic acid, thimerosal, and the like may be further included. In addition, most of the injections may further include an isotonic agent such as sugar or sodium chloride.

Examples of the transdermal delivery agent include ointments, creams, lotions, gels, liquid for external application, pastes, liniments, aerosols, and the like. The transdermal delivery means that the pharmaceutical composition is topically administered to the skin such that an effective amount of the active ingredient included in the pharmaceutical composition is delivered to the skin.

For the inhalants, the compound used according to the present invention may be conveniently delivered in the form of aerosol spray from a pressurized pack or a nebulizer using a suitable propellant, for example, dichlorofluoromethane, trichlorofluoromethane, dichlorotetrafluoroethane, carbon dioxide, or other suitable gases. In the case of pressurized aerosols, a dosage unit may be determined by providing a valve configured to deliver a metered amount. For example, gelatin capsules and cartridges for use in inhalers or blowers may be formulated to include a powder mixture of a compound and a suitable powder base such as lactose or starch. Formulations for parenteral administration are described in the reference, which is a prescription commonly known in all pharmaceutical chemistry (Remington's Pharmaceutical Science, 15th Edition, 1975. Mack Publishing Company, Easton, Pa. 18042, Chapter 87: Blaug, Seymour).

The pharmaceutical composition of the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration route, excretion rate, treatment period, and simultaneously used drugs, and other factors well known in the medical field. The pharmaceutical composition of the present invention may be administered as an individual therapeutic agent or in combination with other therapeutic agents, may be administered sequentially or simultaneously with existing therapeutic agents, and may be administered in a single dose or multiple doses. That is, a total effective amount of the pharmaceutical composition of the present invention may be administered to a patient in a single dose, and may be administered by a fractionated treatment protocol which is administered in multiple doses for a long period of time. It is important to administer the composition in the minimum amount that enables achievement of the maximum effects without side effects in consideration of all the above-described factors, and this may be easily determined by those of ordinary skill in the art.

A dosage of the pharmaceutical composition of the present invention varies depending on the body weight, age, and gender of a patient, health conditions, diet, administration time, administration method, excretion rate, and the severity of disease. A daily dosage thereof may be administered parenterally in an amount of preferably 0.01 mg to 50 mg, more preferably 0.1 mg to 30 mg per body weight (1 kg) based on the ethyl vanillin, and a daily dosage thereof may be administered orally in a single dose or multiple doses in an amount of preferably 0.01 mg to 100 mg, more preferably 0.01 mg to 10 mg per body weight (1 kg), based on the ethyl vanillin of the present invention. However, the dosage may be increased or decreased according to administration route, the severity of obesity, gender, body weight, age, and the like, and thus the dosage is not intended to limit the scope of the present invention in any way.

The pharmaceutical composition of the present invention may be used alone or in combination with surgery, radiation therapy, hormone therapy, chemotherapy, and methods using a biological response modifier.

The pharmaceutical composition of the present invention may also be provided in the form of a formulation for external use, including ethyl vanillin as an active ingredient. When used as a preparation for external application to the skin, the pharmaceutical composition for the prevention or treatment of a muscle disease according to the present invention may further include adjuvants commonly used in dermatology, such as other ingredients commonly used in preparations for external application to the skin, for example, fatty substances, organic solvents, solubilizing agents, thickeners and gelling agents, softeners, antioxidants, suspending agents, stabilizers, foaming agents, fragrances, surfactants, water, ionic or non-ionic emulsifiers, fillers, metal ion blocking agents, chelating agents, preservatives, vitamins, blocking agents, wetting agents, essential oils, dyes, pigments, hydrophilic or lipophilic active agents, lipid vesicles, or the like. In addition, the above-listed ingredients may be introduced in an amount generally used in the dermatology field.

When the pharmaceutical composition for the prevention or treatment of a muscle disease according to the present invention is provided as a dermatologic agent, the preparation may be in the form of a formulation such as ointment, a patch, gel, a cream, an aerosol, or the like, but the present invention is not limited thereto.

Health Functional Food Composition for Muscle Differentiation Promotion, Muscle Regeneration, or Muscle Strengthening The present invention also provides a health functional food composition for preventing or alleviating a muscle disease, comprising ethyl vanillin or a pharmaceutically acceptable salt thereof as an active ingredient.

The present invention also provides a health functional food composition for muscle differentiation promotion, muscle regeneration, or muscle strengthening, comprising ethyl vanillin or a pharmaceutically acceptable salt thereof as an active ingredient.

The present invention also provides a health functional food composition for increasing muscle mass or promoting myogenesis, comprising ethyl vanillin or a pharmaceutically acceptable salt thereof as an active ingredient.

The present invention also provides a health functional food composition for improving muscle function, comprising ethyl vanillin or a pharmaceutically acceptable salt thereof as an active ingredient.

For the ethyl vanillin in the health functional food composition, the detailed description thereof is provided above.

In the health functional food composition for muscle differentiation promotion, muscle regeneration, or muscle strengthening according to the present invention, when used as an additive of a health functional food, the ethyl vanillin may be added to a food directly or in combination with other foods or food ingredients, and may be appropriately used using a general method. The amount of the active ingredient to be mixed may be appropriately determined according to the purpose of use such as prevention, health, treatment, or the like.

Formulations of the health functional food include not only powder, granules, pills, tablets, and capsules, but also any general foods or beverages.

The type of food is not particularly limited and includes all foods in a general sense, and non-limiting examples of foods to which the material may be added may include meat, sausage, bread, chocolate, candies, snacks, confectionaries, pizza, ramen, other noodles, gums, dairy products including ice cream, various soups, beverages, tea, drinks, alcoholic beverages, and vitamin complexes.

Generally, for the preparation of foods or beverages, the ethyl vanillin may be added in an amount of 15 parts by weight or less, preferably 10 parts by weight or less, with respect to 100 parts by weight of raw materials. However, in the case of long-term ingestion for health and hygienic purposes or for health control purposes, the amount may be below the above range, and since the present invention has no safety problem because a fraction from a natural substance is used, the active ingredient may also be used in an amount above the above range.

In the health functional food according to the present invention, a beverage may include additional ingredients such as various flavoring agents, natural carbohydrates, or the like as in general beverages. Examples of the above-described natural carbohydrates include monosaccharides such as glucose and fructose, disaccharides such as maltose and sucrose, polysaccharides such as dextrin and cyclodextrin, and sugar alcohols such as xylitol, sorbitol, erythritol, and the like. As a flavoring agent, a natural flavoring agent such as a thaumatin or stevia extract, a synthetic flavoring agent such as saccharin or aspartame, or the like may be used. The proportion of the natural carbohydrates may range from about 0.01 g to 0.04 g, preferably about 0.02 g to about 0.03 g, with respect to 100 mL of the beverage according to the present invention.

In addition to the above ingredients, the health functional food composition for muscle differentiation promotion, muscle regeneration, or muscle strengthening according to the present invention may include various nutritional supplements, vitamins, electrolytes, flavors, colorants, pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. In addition, the health functional food composition for muscle differentiation promotion, muscle regeneration, or muscle strengthening according to the present invention may include flesh for the preparation of natural fruit juice, fruit juice beverages, and vegetable beverages. These ingredients may be used alone or a combination thereof may be used. The proportion of these additives is not limited, but the amounts of the additives generally range from 0.01 part by weight to 0.1 part by weight with respect to 100 parts by weight of the health functional food of the present invention.

Livestock Feed Composition for Muscle Differentiation Promotion, Muscle Regeneration, or Muscle Strengthening The present invention also provides a livestock feed composition for preventing or alleviating a muscle disease, comprising ethyl vanillin or a pharmaceutically acceptable salt thereof as an active ingredient. Detailed description of the ethyl vanillin is provided above.

The present invention also provides a livestock feed composition for muscle differentiation promotion, muscle regeneration, muscle function improvement, or muscle strengthening, comprising ethyl vanillin or a pharmaceutically acceptable salt thereof as an active ingredient. Detailed description of the ethyl vanillin is described above.

The livestock may be one type of livestock selected from the group consisting of cows, pigs, chickens, ducks, goats, sheep, and horses, but the present invention is not limited thereto.

The feed composition may include a feed additive. The feed additive of the present invention corresponds to a feed supplement in the Feed Control Act.

As used herein, the term "feed" may refer to any natural or artificial diet, meal, or the like, or components of such meal intended or suitable to be eaten, taken in, or digested by animals.

The type of feed is not particularly limited, and any feed generally used in the art may be used. Non-limiting examples of the feed may include plant-based feed, such as grains, nuts, food by-products, seaweeds, fibers, drug by-products, fats and oils, starches, gourds, and grain by-products; and animal-based feed such as proteins, inorganic matter, fats and oils, minerals, single cell proteins, animal plankton, and foods. These may be used alone or a mixture of two or more thereof may be used.

In addition, the feed additive may further include a carrier accepted by a unit animal. In the present invention, the feed additive may be added as it is or a carrier, a stabilizer, and the like may be added thereto, and various nutrients such as vitamins, amino acids, minerals, and the like, antioxidants, other additives, and the like may be added according to need, and the form thereof may be in a suitable state such as powder, a granule, a pellet, a suspension, or the like. The feed additive of the present invention may be supplied alone or in combination with feed to a unit animal.

Cosmetic Composition for Improving Muscle Function

The present invention also provides a cosmetic composition for improving muscle function, comprising ethyl vanillin or a pharmaceutically acceptable salt thereof as an active ingredient. The cosmetic composition is not particularly limited, but may be used for external applications to the skin or may be orally ingested.

The composition for improving muscle function according to the present invention may also be a cosmetic composition. The cosmetic composition of the present invention includes ethyl vanillin as an active ingredient, and may be prepared with a dermatologically acceptable excipient, in the form of a basic cosmetic composition (cleansers such as a skin lotion, a cream, an essence, a cleansing foam, and cleansing water, packs, and body oils), a color cosmetic composition (foundations, lipsticks, mascara, and makeup bases), a hair product composition (shampoos, hair conditioners, and hair gels), soaps, and the like.

The excipients may include, but are not limited to, for example, emollients, skin penetration enhancers, colorants, fragrances, emulsifiers, thickeners, and solvents. In addition, the excipients may further include fragrances, pigments, fungicides, antioxidants, preservatives, moisturizing agents, and the like, and may include thickeners, inorganic salts, synthetic polymer materials, and the like for the purpose of improving physical properties. For example, cleansers and soaps may be easily prepared using the cosmetic composition of the present invention by adding the ethyl vanillin to a general cleanser and a soap base. Creams may be prepared by adding ethyl vanillin or a salt thereof to a general cream base in an oil-in-water (O/W) state. Fragrances, chelating agents, pigments, antioxidants, preservatives, and the like, and synthetic or natural substances such as proteins, minerals, vitamins, and the like, which are used to improve physical properties, may further be added thereto.

The amount of ethyl vanillin included in the cosmetic composition of the present invention ranges from, but is not limited to, preferably 0.001 wt % to 10 wt %, more preferably 0.01 wt % to 5 wt %, with respect to a total weight of the composition. When the amount of ethyl vanillin is less than 0.001 wt %, a desired anti-aging or wrinkle-improving effect cannot be expected, and when the amount of ethyl vanillin is greater than 10 wt %, there may be difficulties in safety or preparation of formulations.

The present invention also provides a method of preventing or treating a muscle disease, promoting muscle differentiation, regenerating muscles, or strengthening muscles, including administering, to a subject, a pharmaceutical composition including ethyl vanillin or a salt thereof as an active ingredient, or allowing it to be taken.

The present invention also provides a use of a composition for preventing or treating a muscle disease, promoting muscle differentiation, regenerating muscles, or strengthening muscles, the composition including ethyl vanillin or a salt thereof as an active ingredient.

As described above, the composition of the present invention comprising ethyl vanillin or a pharmaceutically acceptable salt thereof as an active ingredient may increase the phosphorylation of the 4E-BP1 protein and the p70S6K1 protein in myoblasts and inhibit the gene expression of MuRF1 and MaFbx/atrogin 1, thereby exhibiting a muscle strengthening effect through muscle differentiation, muscle regeneration, and an increase in muscle mass in muscle diseases caused by muscle dysfunction, muscle wasting, or muscle degeneration, and may inhibit muscle loss. Thus, the composition may be used to prevent or treat a muscle disease, promote muscle differentiation, regenerate muscles, and increase muscle mass or improve muscle function.

Hereinafter, the present invention will be described in further detail with reference to the following examples and preparation examples. It will be obvious to those of ordinary skill in the art that these examples and preparation examples are provided for illustrative purposes only and are not intended to limit the scope of the present invention.

EXAMPLES

Example 1

Confirmation of Effect of Ethyl Vanillin on Inhibiting Muscle Loss Using Mouse Myoblasts To confirm the effect of ethyl vanillin on inhibiting muscle loss, muscle damage was induced in myotubes, the differentiation of which was induced from mouse myoblasts, and the myotubes were treated with ethyl vanillin to examine the degree of damage to the myotubes.

1-1. Cell Culture

First, differentiation of myotubes from mouse myoblasts was induced. A mouse myoblast cell line (C2C12 cells) was purchased from ATCC (Manassas, Va., USA) and used. The purchased cells were inoculated in 10% fetal bovine serum media (Gibco-BRL) and incubated in a 5% $CO_2$ incubator at 37° C. When the confluency of the cells attached to the media became 80% or higher, the cells were transferred to 2% horse serum media (Gibco-BRL) to differentiate myoblasts into myotubes.

1-2. Muscle Damage Induction

For two days (48 hours) from day 4 after differentiation into myotubes started to be induced, the media were treated with 50 μM dexamethasone (dexa; Sigma Aldrich, USA) to induce muscle reduction. To confirm a muscle loss inhibition effect according thereto, the media were treated with 100 μM ethyl vanillin (CAS No. 112-31-2, Sigma Aldrich, USA) along with dexamethasone and incubated. As a non-treated control, cells treated with only dexamethasone and not treated with ethyl vanillin were used.

1-3. Measurement of Thickness of Myotubes

After completion of the incubation, the cells were washed twice with phosphate buffered saline (PBS), and then fixed by treatment with 100% methanol for 10 minutes. When the fixing was completed, the cells were naturally dried at room temperature for 10 minutes, and then a Giemsa-Wright staining solution (Asan Pharmaceutical, Seoul), which specifically stains myotubes, was dropped onto the cells and the cells were left at room temperature for 30 minutes to stain the cells.

The stained myotubes were photographed using a fluorescence microscope (IX 71, Olympus) at a magnification of 10×, and then analyzed using image J software (USA). Six sections were randomly selected from each well and micrographed, and the thickness of at least 100 myotubes from each well was analyzed (three repetitions/group).

1-4. Experimental Results

Figure 1:
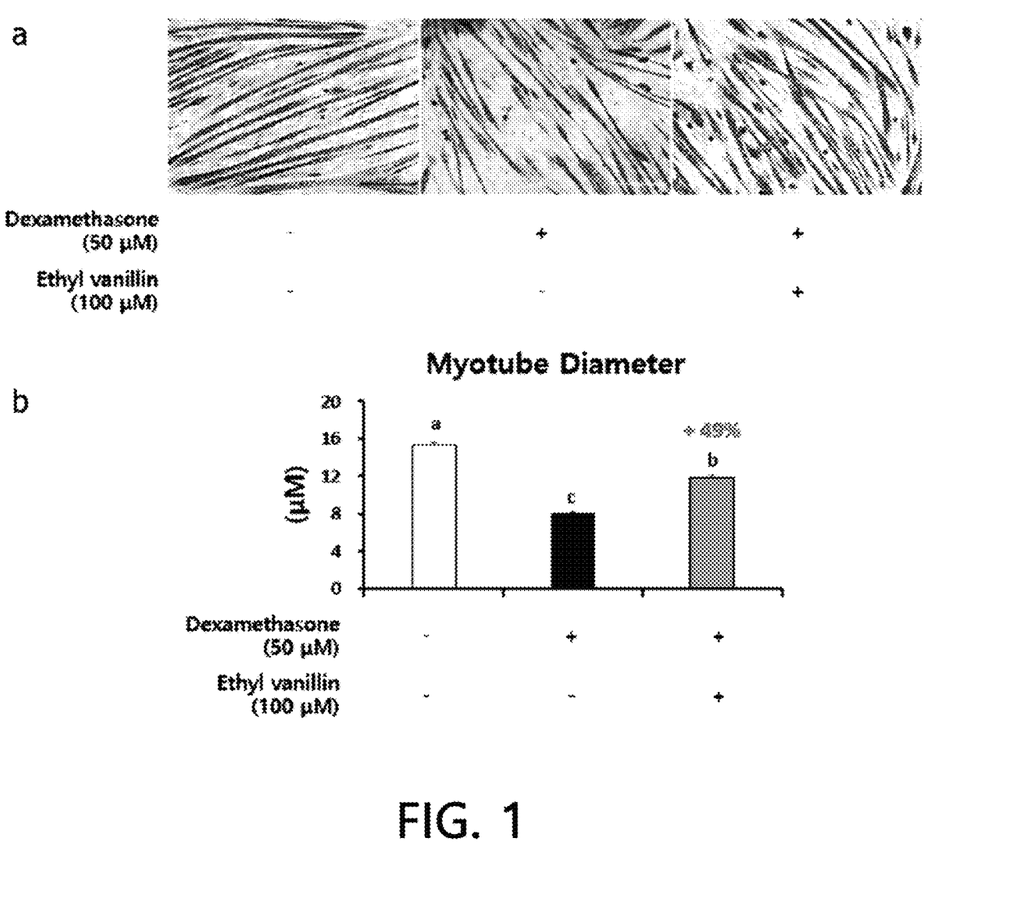
FIG. 1 illustrates changes in thickness of myotubes of mouse myoblasts.

As a result of examining a protective effect by ethyl vanillin in myotubes differentiated from mouse myoblasts, it was confirmed that, in a non-treated control (Dexa) treated with dexamethasone alone, the thickness of myotubes was significantly reduced compared to normal cells (Basal, not treated with dexamethasone), and when treated with ethyl vanillin, the thickness of the myotubes reduced by dexamethasone could be increased (see FIG. 1A). When quantitatively quantified, a +49% increase effect was exhibited by treatment with ethyl vanillin compared to a reduction in myotubes caused by dexamethasone (see FIG. 1B). Thus, it was confirmed that ethyl vanillin could inhibit muscle loss and promote muscle growth by increasing the thickness of myotubes derived from mouse myoblasts.

Example 2

Verification of Action Mechanism of Effect of Ethyl Vanillin on Protecting Muscles Since it was confirmed that ethyl vanillin could inhibit muscle loss and promote muscle growth by protecting myotubes, to confirm via which pathway ethyl vinyl is capable of exhibiting a muscle protective effect in cells, changes in expression level of representative molecules associated with protein synthesis were examined.

2-1. Confirmation of Changes in mRNA Expression Level through RNA Extraction and RT-PCR Differentiation of myotubes from myoblasts was induced in the same manner as in Example 1, and the cells were treated with dexamethasone and/or ethyl vanillin and incubated. After completing the incubation of all experimental groups and the control, cells of each group were obtained, 334 μl of a TRIzol solution per 1×10⁷ myotubes was added and replaced, followed by centrifugation at 12,000×g and 4° C. for 10 minutes. Thereafter, the supernatant was transferred to a new tube and 67 μl of chloroform was added thereto, followed by mixing by vortexing. The supernatant in the mixed solution was transferred again to a new tube, and isopropanol was added thereto in a ratio of 1:1 (v:v) of isopropanol to supernatant, followed by vigorous shaking about 10 times and being left at room temperature for 15 minutes. Once again, centrifugation was carried out at 12,000×g and 4° C. for 10 minutes to remove a supernatant, and 1 ml of 70% ethanol was added to the precipitate, followed by centrifugation at 7,500×g and 4° C. for 5 minutes to remove the ethanol, and the tubes were dried at room temperature for 15 minutes. Finally, precipitated RNA was dissolved in nuclease free water to obtain RNA extracted from the cells. The concentration of RNA was identified by measuring absorbance at wavelengths of 260 nm and 280 nm using a UV/VIS spectrometer, and was subjected to electrophoresis to confirm the integrity of RNA samples.

Reverse transcription-polymerase chain reaction (RT-PCR) was performed using the prepared RNA samples. The obtained RNA samples were used as templates and reverse transcription was performed using oligo dT primers and SuperScript Reverse Transcriptase (GIBCO BRL, Gaithersburg, Md., USA) to synthesize cDNA. The synthesized cDNA was used as a template and PCR was performed using primer pairs (forward primers and reverse primers) shown in Table 1 below. Each primer was constructed based on the 5' and 3' flanking sequence of cDNA of the template gene to be amplified. After PCR was completed, 1 μl of each amplified PCR product was subjected to electrophoresis on agarose gel to confirm generated DNA bands.

buffer, a 100 mM Tris-HCl buffer solution (pH 7.4) containing 5 mM EDTA, 50 mM sodium pyrophosphate, 50 mM NaF, 100 mM orthovanadate, 1% Triton X-100, 1 mM phenylmethanesulfonyl fluoride (PMSF), 2 g/mL of aprotinin, 1 μg/mL of pepstatin A, and 1 μg/mL of leupeptin was used. After lysing the cells, the lysates were obtained, and then centrifuged at 1,300×g and 4° C. for 20 minutes, and then the middle layer was taken as a protein layer in the cell extract. For the protein layer, the concentrations of proteins were quantified by the Bradford method.

40 μg of the quantified proteins were electrophoresed by SDS-PAGE, and then the separated proteins were transferred to nitrocellulose membranes (Amersham, Buckinghamshire, UK). Then, the membranes were washed three times for 10 minutes using a Tris-buffered saline and Tween 20 solution (TBS-T), followed by blocking using 10% skim milk for 60 minutes. Primary antibodies diluted in a ratio of 1:1,000 were added to the blocked membranes, and gently shaken at 4° C. for 12 hours, allowing the antibodies to bind to the proteins, followed by washing using TBS-T, and secondary antibodies diluted in a ratio of 1:2,000 were added thereto, allowing the secondary antibodies to bind to the primary antibodies for 60 minutes, followed by washing. At this time, as the primary antibodies, p70S6K1, phopho-p70S6K1 (p-p70S6K1), 4E-BP1, phospho-4E-BP1 (p-4E-BP1), and GAPDH (Cell Signaling Technology, Beverly, Mass., USA) were used. Finally, the proteins bound to the antibodies were visualized on X-ray film using an ECL western blot detection kit (RPN2106, Amersham, Arlington Heights, Ill., USA). Bands visualized on the X-ray film were scanned and quantified using Quantity One analysis software (Bio-Rad).

2-3. Experimental Results

Changes in expression of molecules related to protein synthesis and degradation by ethyl vanillin were confirmed in mouse myoblasts as a target. In control cells (Dexa), compared to normal cells (Basal), the amounts of the p-4E-BP1 protein and the p-p70S6K1 protein, which are associ-

TABLE 1

Primer sequences used in RT-PCR

| Target gene | Primer direction | Sequence (5'→3') | | Tm (° C.) | Length of PCR product (bp) |
|---|---|---|---|---|---|
| MaFbx (synonym: atrogin-1) | F<br>R | GTCCAGAGAGTCGGCAAGTC<br>GTCGGTGATCGTGAGACCTT | (SEQ ID NO. 1)<br>(SEQ ID NO. 2) | 63 | 141 |
| MuRF1 (synonym: TRAM63) | F<br>R | ACATCTACTGTCTCACGTGT<br>TGTCCTTGGAAGATGCTTTG | (SEQ ID NO. 3)<br>(SEQ ID NO. 4) | 58 | 106 |
| Myostatin | F<br>R | TCACGCTACCACGGAAACAA<br>AGGAGTCTTGACGGGTCTGA | (SEQ ID NO. 5)<br>(SEQ ID NO. 6) | 60 | 166 |
| IGF | F<br>R | GGGGACTTTCGTGACTGAGC<br>GGTAGGTCCGGGTCGTTTAC | (SEQ ID NO. 7)<br>(SEQ ID NO. 8) | 60 | 165 |
| GAPDH | F<br>R | GTGATGGCATGGACTGTGGT<br>GGAGCCAAAAGGGTCATCAT | (SEQ ID NO. 9)<br>(SEQ ID NO. 10) | 55 | 163 |

Figure 2:
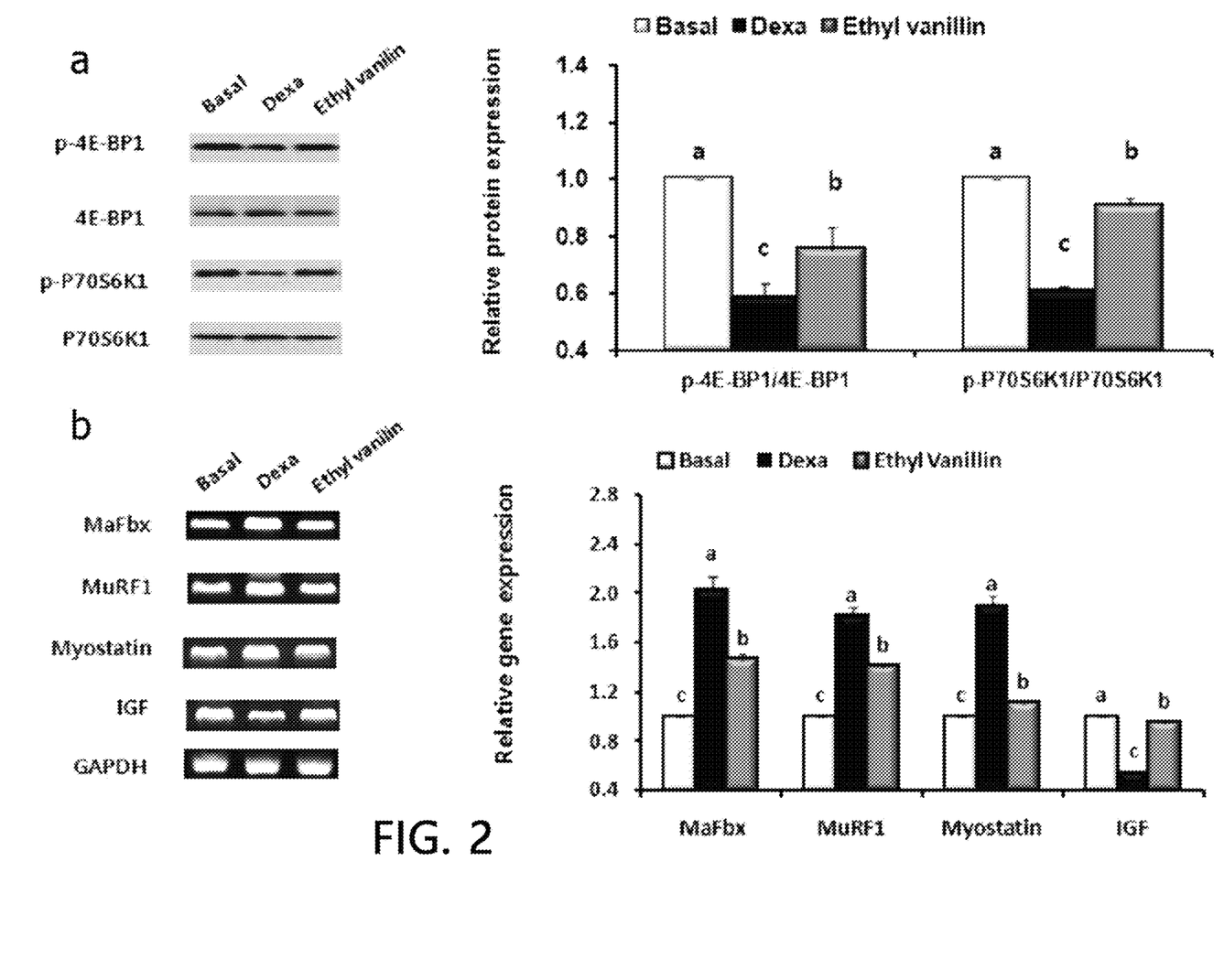
FIG. 2 illustrates the results of confirming changes in mRNA expression levels (A) and protein expression levels (B) of proteolysis- and protein synthesis-related molecules in mouse myoblasts treated with ethyl vanillin.

2-2. Confirmation of Changes in Protein Expression level through Western Blotting Differentiation of myotubes from myoblasts was induced in the same manner as in Example 1, and the cells were treated with dexamethasone and/or ethyl vanillin and incubated. After completing the incubation of all experimental groups and the control, the media were removed and a lysis buffer was added to each well to lyse the cells. As the lysis ated with protein synthesis, were significantly reduced, whereas the expression of MaFbx/atrogin 1 and MuRF1, which are protein degradation genes, was significantly increased. Treatment with ethyl vanillin significantly increased the amounts of the p-4EBP1 and p-p70S6K1 proteins reduced by dexamethasone, while significantly reducing the expression of MaFbx/stroginl, MuRF1, and Myostatin (see FIG. 2). Thus, it may be determined that ethyl vanillin increases the phosphorylation of the 4E-BP1 and p70S6K1 proteins in mouse myoblasts, and inhibits the gene expression of MaFbx/atrogin1, MuRF1, and Myostatin, and thus may be ultimately involved in increasing muscle mass.

Example 3

Efficacy of Ethyl Vanillin on Muscle Strengthening Using Mice

Changes in muscle strength were examined when experimental animals were fed a diet containing ethyl vanillin.

3-1. Experimental Method

1) Experimental Diet Preparation and Breeding of Laboratory Animals 24 5-week-old male C57BL/6N mice (Mating, Korea) were adapted to a laboratory environment for one week with a commercial normal diet (rodent chow), and then randomly divided into three groups each containing 8 mice (Chow group, HFD group, and Ethyl vanillin group) according to a randomized block design and bred for 10 weeks. An obesity-inducing diet used in the present experiment is a high-fat diet (HFD: 40% fat calorie, 17 g lard+3% corn oil/100 g diet), and an ethyl vanillin-supplemented high-fat diet (Ethyl vanillin) has the same composition as that of the HFD, but contained 0.2% ethyl vanillin (see Table 2). A normal diet group (Chow) was fed commercial rodent chow. Ethyl vanillin was purchased from Sigma-Aldrich.

TABLE 2

Experimental Diet Composition List

| Component | High-fat diet (HFD) (g/kg diet) | Ethyl vanillin-supplemented diet (g/kg diet) |
| --- | --- | --- |
| Casein | 200 | 200 |
| DL-methionine | 3 | 3 |
| Corn starch | 111 | 109 |
| Sucrose | 370 | 370 |
| Cellulose | 50 | 50 |
| Corn oil | 30 | 30 |
| Lard | 170 | 170 |
| Vitamin complex | 12 | 12 |
| Mineral complex | 42 | 42 |
| Choline bitartrate | 2 | 2 |
| Cholesterol | 10 | 10 |
| Tert-butylhydroquinone | 0.04 | 0.04 |
| Experimental material (ethyl vanillin) | — | 2 |
| Total (g) | 1,000 | 1,000 |

2) Grip Test

To measure the grip strength of mice, grip strength was measured using four feet of the mice at week 10 of breeding. A force (N) for mice to hold a wire mesh was measured a total of five times using a grip strength measurer equipped with a wire mesh (20×10 cm) (Daejong Instrument Industry Co., Ltd., Korea), and a rest period of 1 minute or longer was given between measurements. Experimental results were obtained by dividing the measured force (N) by body weight (kg).

3) Four Limb Hanging Test

To measure the limb muscle strength of mice, the time that the mice hung upside down using their four feet was measured at week 10 of breeding. The time (seconds) that the mice hung upside down in a cage equipped with a wire mesh cover (diameter<0.5 cm) (20×30×50 cm, Jeung-Do Bio & Plant Co., Ltd, Korea) was measured a total of three times, and a rest period of 30 minutes or longer was given between measurements. Experimental results were obtained by multiplying hanging time (sec) by body weight (kg).

4) Immunohistochemical Staining of Muscle Tissue

Muscle tissues of mice were extracted, fixed in 10% formalin, and then stained with hematoxylin and eosin (H&E) after requesting Korea CFC (Gyeonggi-do, Korea) to do so, and observed using an optical microscope (IX71, Olympus, JPN) and photographed using a digital camera (DP71, Olympus, JPN).

5) Statistical Analysis

The statistical analysis of all data was performed using the Statistical Package for the Social Sciences (SPSS version 21.0, IBM, Armonk, N.Y., USA), and analysis values were expressed as mean±SEM, and a significant difference between groups was verified by ANOVA.

3-2. Experimental Results

Figure 3:
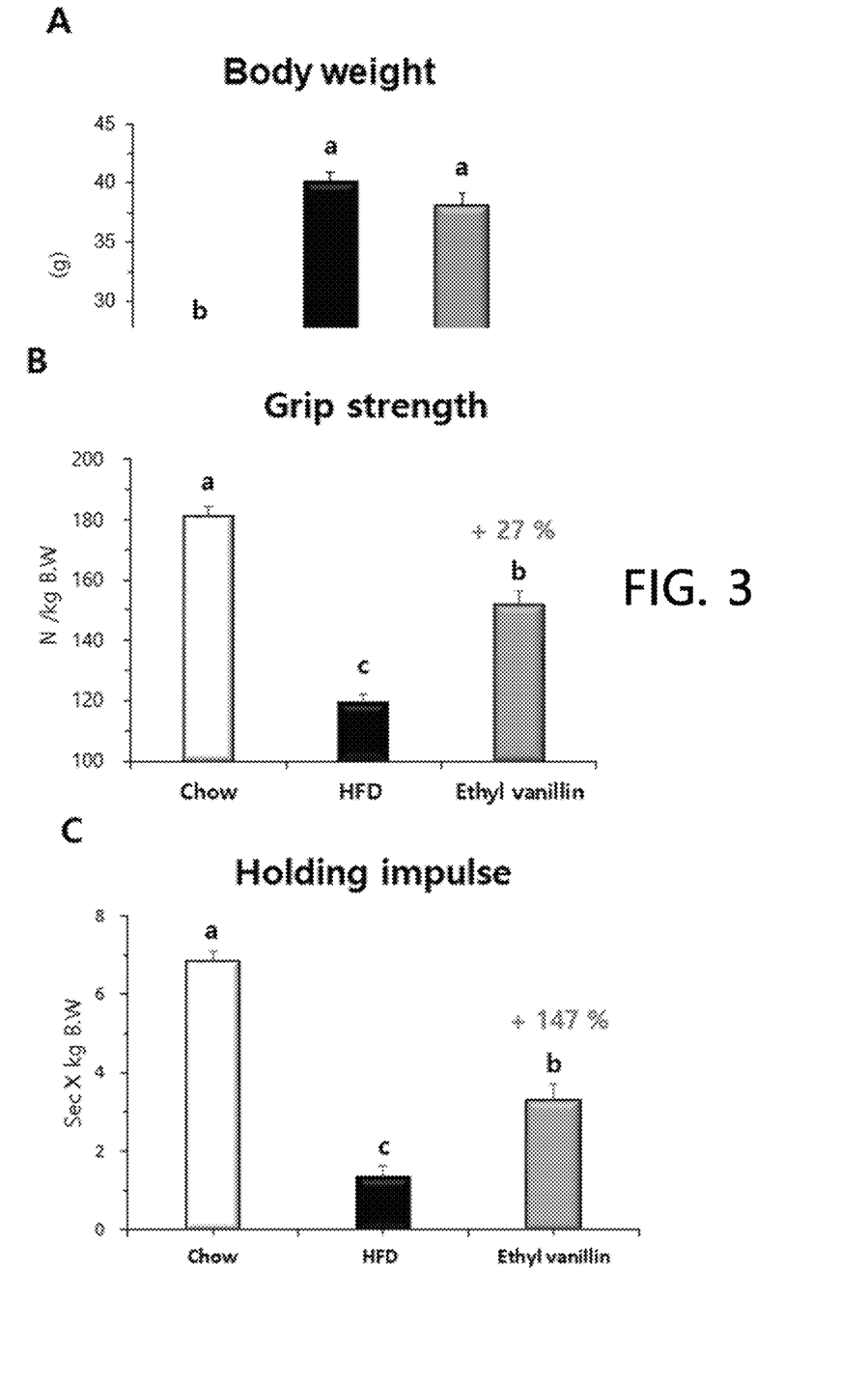
FIG. 3 illustrates the results of confirming an increase in muscular strength caused by ingestion of ethyl vanillin, from changes in body weight (A), grip strength (B), and holding impulse (C) of a normal feed group (Chow), a high-fat diet (HFD) group, and mice fed ethyl vanillin.

1) Confirmation of Increase in Muscle Strength of Mice by Administration of Ethyl Vanillin There was no significant difference between the body weights of mice fed ethyl vanillin and the body weights of mice fed a high-fat diet (see FIG. 3A). Ethyl vanillin significantly increased the grip strength (see FIG. 3B) and holding impulse (see FIG. 3C) of mice fed a high-fat diet by 27% and 147%, respectively. Thus, it was confirmed that ethyl vanillin exhibited an excellent effect of increasing muscle strength in an animal model with high-fat-diet-induced muscle loss.

2) Changes in Fiber Diameter of Mouse Muscle Tissue by Intake of Ethyl Vanillin

Figure 4:
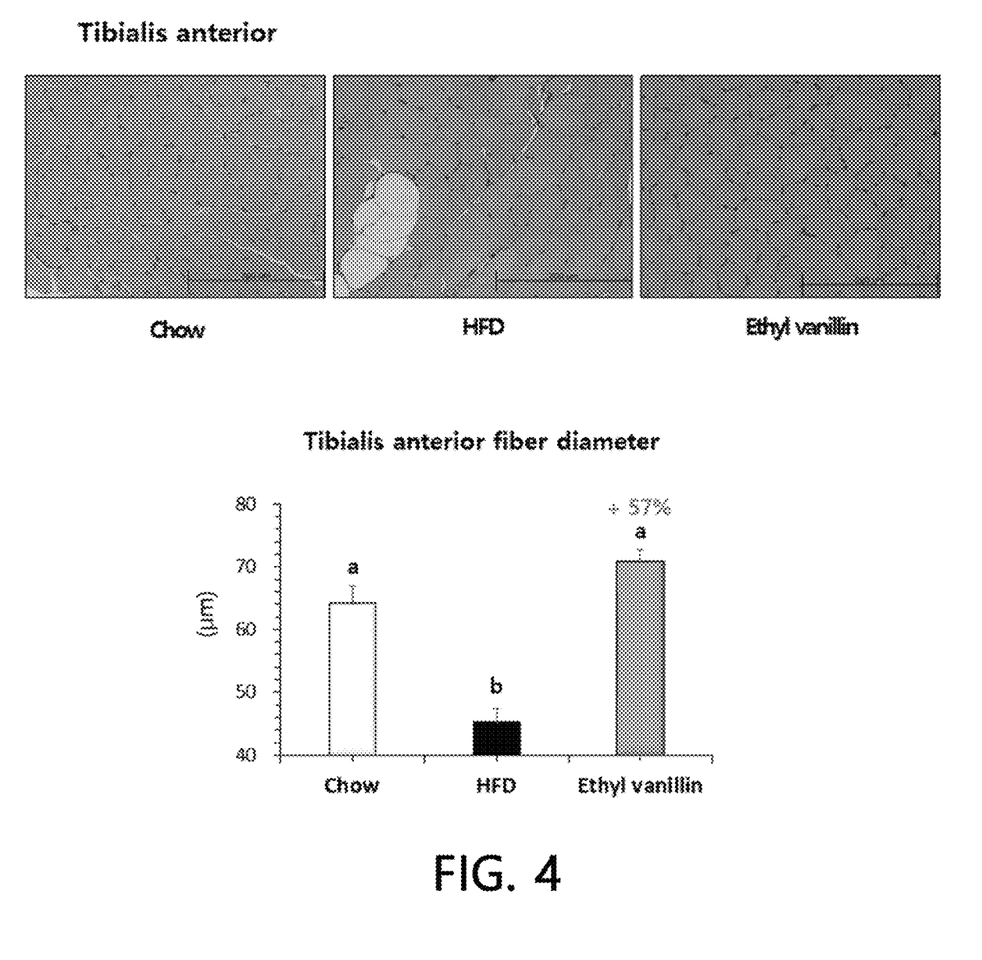
FIG. 4 illustrates the results of confirming the tibialis anterior fiber diameter of muscle tissues of mice fed ethyl vanillin, wherein quantitative values represent the fiber diameter of the muscle of each of 8 mice as mean±standard error, and p<0.05 indicates statistical significance.

Ethyl vanillin significantly increased the fiber diameter of the tibialis anterior (57%, FIG. 4) of mice fed a high-fat diet. Thus, it was confirmed that ethyl vanillin exhibited an excellent effect of increasing skeletal muscles in an animal model with high-fat-diet-induced muscle loss.

MODE OF INVENTION

Hereinafter, preparation examples of pharmaceuticals, foods, cosmetics including the ethyl vanillin as an active ingredient according to the present invention will be described, but are provided for illustrative purposes only and are not intended to limit the present invention. Pharmaceuticals, foods, or cosmetic compositions of Preparation Examples 1 to 4 were prepared using a general method using the extracts having an excellent effect of preventing or treating muscle diseases or improving muscle function in accordance with compositions and composition ratios described below.

Preparation Example 1

Preparation of Pharmaceutical Compositions

<1-1> Preparation of Powder

| Ethyl vanillin | 20 mg |
| --- | --- |
| Lactose hydrate | 100 mg |
| Talc | 10 mg |

The above ingredients were mixed and put into an airtight bag, thereby completing the preparation of powder.

<1-2> Preparation of Tablets

| Ethyl vanillin | 10 mg |
|---|---|
| Corn starch | 100 mg |
| Lactose hydrate | 100 mg |
| Magnesium stearate | 2 mg |

The above ingredients were mixed and then tablets were prepared using a general tablet preparation method.

<1-3> Preparation of Capsules

| Ethyl vanillin | 10 mg |
|---|---|
| Microcrystalline cellulose | 3 mg |
| Lactose hydrate | 14.8 mg |
| Magnesium stearate | 0.2 mg |

The above ingredients were mixed, and then gelatin capsules were filled therewith using a general capsule preparation method, thereby completing the preparation of capsules.

<1-4> Preparation of Injections

| Ethyl vanillin | 10 mg |
|---|---|
| Mannitol | 180 mg |
| Sterile distilled water for injection | 2,974 mg |
| Dibasic sodium phosphate | 26 mg |

The above ingredients were mixed, and then an injection was prepared in the above-described content per 1 ampoule (2 mL) according to a general injection preparation method.

<1-5> Preparation of Liquids

| Ethyl vanillin | 10 mg |
|---|---|
| Isomerized sugar | 10 mg |
| Mannitol | 5 mg |
| Purified water | appropriate amount |
| Lemon flavor | appropriate amount |

The above ingredients were added to purified water and dissolved therein according to a general liquid preparation method, and an appropriate amount of a lemon flavor was added thereto, and then purified water was added to the resulting solution to adjust a total amount to 100 mL, and then a brown vial was filled with the resulting mixture and sterilized, thereby completing the preparation of a liquid.

Preparation Example 2

Preparation of Health Foods

<2-1> Preparation of Health Supplement Foods

| Ethyl vanillin | 10 mg |
|---|---|
| Vitamin mixture | appropriate amount |
| Vitamin A acetate | 70 μg |
| Vitamin E | 1.0 mg |
| Vitamin B$_1$ | 0.13 mg |
| Vitamin B$_2$ | 0.15 mg |
| Vitamin B$_6$ | 0.5 mg |
| Vitamin B$_{12}$ | 0.2 μg |
| Vitamin C | 10 mg |
| Biotin | 10 μg |
| Nicotin acid amide | 1.7 mg |
| Folic acid | 50 μg |
| Calcium pantothenate | 0.5 mg |
| Mineral mixture | appropriate amount |
| Ferrous sulfate | 1.75 mg |
| Zinc oxide | 0.82 mg |
| Magnesium carbonate | 25.3 mg |
| Monobasic potassium phosphate | 15 mg |
| Dibasic calcium phosphate | 55 mg |
| Potassium citrate | 30 mg |
| Calcium carbonate | 100 mg |
| Magnesium chloride | 24.8 mg |

Although ingredients relatively suitable for use in health foods are mixed in the above-described composition ratio of the vitamin and mineral mixture as an exemplary embodiment, the mixing ratio may be arbitrarily varied, and the above-listed ingredients may be mixed according to a general health food preparation method, and then prepared into granules, which may then be used for the preparation of a health food composition according to a general method.

<2-2> Preparation of Health Drinks

| Ethyl vanillin | 10 mg |
|---|---|
| Vitamin C | 15 g |
| Vitamin E (powder) | 100 g |
| Iron lactate | 19.75 g |
| Zinc oxide | 3.5 g |
| Nicotinic acid amide | 3.5 g |
| Vitamin A | 0.2 g |
| Vitamin B$_1$ | 0.25 g |
| Vitamin B$_2$ | 0.3 g |
| Purified water | appropriate amount |

The above-listed ingredients are mixed according to a general method of preparing a health drink, the mixture is heated and stirred at 85° C. for about 1 hour to prepare a solution, the solution is filtered, the filtrate is collected in a 2 L sterilized container and then sealed and sterilized, followed by refrigerated storage, which is then used for the preparation of a heath drink composition according to the present prevention.

Although ingredients relatively suitable for use in favorite beverages are mixed in the above-described composition ratio as an exemplary example, the mixing ratio may be arbitrarily varied depending on local and national preferences such as demand classes, demand countries, purposes of use, and the like.

Preparation Example 3

Preparation of Cosmetic Compositions

Hereinafter, preparation examples of cosmetic compositions including the extract of the present invention will be described, but are provided for illustrative purposes only and are not intended to limit the present invention.

<3-1> Nourishing Face Lotion (Milk Lotion)

| Ethyl vanillin | 2.0 wt % |
|---|---|
| Squalane | 5.0 wt % |
| Beeswax | 4.0 wt % |
| Polysorbate 60 | 1.5 wt % |
| Sorbitan sesquioleate | 1.5 wt % |
| Liquid paraffin | 0.5 wt % |
| Caprylic/capric triglyceride | 5.0 wt % |
| Glycerin | 3.0 wt % |
| Butylene glycol | 3.0 wt % |

| | |
|---|---|
| Propylene glycol | 3.0 wt % |
| Carboxyvinyl polymer | 0.1 wt % |
| Triethanolamine | 0.2 wt % |
| Preservative, pigment, fragrance | appropriate amounts |
| Purified water | to 100 wt % |

Although ingredients relatively suitable for use in nourishing face lotions are mixed in the above-described composition ratio as an exemplary embodiment, the mixing ratio may be arbitrarily varied, and the nourishing face lotion may be prepared according to a general preparation method used in the cosmetic field.

<3-2> Skin Softener (Skin Lotion)

| | |
|---|---|
| Ethyl vanillin | 2.0 wt % |
| Glycerin | 3.0 wt % |
| Butylene glycol | 2.0 wt % |
| Propylene glycol | 2.0 wt % |
| Carboxyvinyl polymer | 0.1 wt % |
| PEG12 nonylphenyl ether | 0.2 wt % |
| Polysorbate 80 | 0.4 wt % |
| Ethanol | 10.0 wt % |
| Triethanolamine | 0.1 wt % |
| Preservative, pigment, fragrance | appropriate amounts |
| Purified water | to 100 wt % |

Although ingredients relatively suitable for use in skin softeners are mixed in the above-described composition ratio as an exemplary embodiment, the mixing ratio may be arbitrarily varied, and the skin softener may be prepared according to a general preparation method used in the cosmetic field.

<3-3> Nourishing Cream

| | |
|---|---|
| Ethyl vanillin | 2.0 wt % |
| Polysorbate 60 | 1.5 wt % |
| Sorbitan sesquioleate | 0.5 wt % |
| PEG60 hydrogenated castor oil | 2.0 wt % |
| Liquid paraffin | 10 wt % |
| Squalane | 5.0 wt % |
| Caprylic/capric triglyceride | 5.0 wt % |
| Glycerin | 5.0 wt % |
| Butylene glycol | 3.0 wt % |
| Propylene glycol | 3.0 wt % |
| Triethanol amine | 0.2 wt % |
| Preservative | appropriate amount |
| Pigment | appropriate amount |
| Fragrance | appropriate amount |
| Purified water | to 100 wt % |

Although ingredients relatively suitable for use in nourishing creams are mixed in the above-described composition ratio as an exemplary embodiment, the mixing ratio may be arbitrarily varied, and the nourishing cream may be prepared according to a general preparation method used in the cosmetic field.

<3-4> Massage Cream

| | |
|---|---|
| Ethyl vanillin | 1.0 wt % |
| Beeswax | 10.0 wt % |
| Polysorbate 60 | 1.5 wt % |
| PEG60 hydrogenated castor oil | 2.0 wt % |
| Sorbitan sesquioleate | 0.8 wt % |
| Liquid paraffin | 40.0 wt % |
| Squalane | 5.0 wt % |
| Caprylic/capric triglyceride | 4.0 wt % |
| Glycerin | 5.0 wt % |
| Butylene glycol | 3.0 wt % |
| Propylene glycol | 3.0 wt % |
| Triethanol amine | 0.2 wt % |
| Preservative, pigment, fragrance | appropriate amounts |
| Purified water | to 100 wt % |

Although ingredients relatively suitable for use in massage creams are mixed in the above-described composition ratio as an exemplary embodiment, the mixing ratio may be arbitrarily varied, and the massage cream may be prepared according to a general preparation method used in the cosmetic field.

<3-5> Pack

| | |
|---|---|
| Ethyl vanillin | 1.0 wt % |
| Polyvinyl alcohol | 13.0 wt % |
| Sodium carboxymethyl cellulose | 0.2 wt % |
| Glycerin | 5.0 wt % |
| Allantoin | 0.1 wt % |
| Ethanol | 6.0 wt % |
| PEG 12 nonyl phenyl ether | 0.3 wt % |
| Polysorbate 60 | 0.3 wt % |
| Preservative, pigment, flavor | appropriate amounts |
| Purified water | to 100 wt % |

Although ingredients relatively suitable for packs are mixed in the above-described mixing ratio as an exemplary example, the mixing ratio may be arbitrarily modified, and the pack may be prepared according to a general preparation method in the cosmetic field.

<3-6> Gel

| | |
|---|---|
| Ethyl vanillin | 0.5 wt % |
| Sodium ethylenediamineacetate | 0.05 wt % |
| Glycerin | 5.0 wt % |
| Carboxyvinyl polymer | 0.3 wt % |
| Ethanol | 5.0 wt % |
| PEG60 hydrogenated castor oil | 0.5 wt % |
| Triethanolamine | 0.3 wt % |
| Preservative, pigment, flavor | appropriate amounts |
| Purified water | to 100 wt % |

Although ingredients relatively suitable for gels are mixed in the above-described mixing ratio as an exemplary example, the mixing ratio may be arbitrarily modified, and the gel may be prepared according to a general preparation method in the cosmetic field.

Although ingredients relatively suitable for cosmetic compositions are mixed in the above-described mixing ratio as an exemplary example, these may be applied to cosmetics for various applications including color cosmetics, and may be used in the preparation of a medicine that can be applied thinly on the human body according to the efficacy thereof, and the mixing ratio may be arbitrarily varied depending on local and national preferences such as demand classes, demand countries, purposes of use, and the like.

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described embodiments should be construed as being provided for illustrative purposes only and not for purposes of limitation

The invention claimed is:

1. A method for treating a muscle disease, the method comprising administering to a subject in need thereof, a composition including ethyl vanillin or a pharmaceutically acceptable salt thereof as an active ingredient to treat the muscle disease, wherein the muscle disease is atony, muscular atrophy, or sarcopenia.

2. The method of claim 1, wherein the subject in need thereof has reduced expression of p-4E-BP1 and p-p70S6K1 proteins, and wherein the composition increases the expression of p-4E-BP1 and p-p70S6K1 proteins in the subject.

3. The method of claim 1, wherein the subject in need thereof has increased expression of muscle RING-finger protein-1 (MuRF1), muscle atrophy F-box (MaFbx), or myostatin, and wherein the composition reduces the expression of muscle RING-finger protein-1 (MuRF1), muscle atrophy F-box (MaFbx), or myostatin in the subject.

4. The method of claim 1, wherein the muscle disease comprises atony.

5. The method according to claim 1, wherein the composition is a pharmaceutical composition, a health functional food composition, or a livestock feed composition.

6. A method of promoting muscle differentiation, regenerating a muscle, improving muscle function, or strengthening a muscle in a subject in need thereof, the method comprising administering, to the subject, a composition comprising ethyl vanillin or a salt thereof as an active ingredient, wherein 0.01 milligrams (mg) to 50 mg per body weight (1 kilogram) of the ethyl vanillin or a salt thereof is administered to the subject.

7. The method according to claim 6, wherein the composition is a pharmaceutical composition, a health functional food composition, or a livestock feed composition.

8. The method of claim 1, wherein the muscle disease comprises muscular atrophy.

9. The method of claim 1, wherein the muscle disease comprises sarcopenia.

10. The method of claim 1, wherein the composition is administered orally.

11. The method of claim 1, wherein the composition is administered parenterally.

12. The method of claim 1, wherein 0.01 milligrams (mg) to 50 mg per body weight (1 kilogram) of the ethyl vanillin is administered to the subject.

13. The method of claim 6, wherein the composition is administered orally.

14. The method of claim 6, wherein the composition is administered parenterally.

* * * * *